US008476026B2

(12) United States Patent
Alex et al.

(10) Patent No.: US 8,476,026 B2
(45) Date of Patent: Jul. 2, 2013

(54) BIOMARKERS OF OVARIAN CANCER

(75) Inventors: Ng Alex, Newton, MA (US); Brian Liu, Somerville, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 188 days.

(21) Appl. No.: 12/935,210

(22) PCT Filed: Mar. 20, 2009

(86) PCT No.: PCT/US2009/001776
§ 371 (c)(1),
(2), (4) Date: Sep. 28, 2010

(87) PCT Pub. No.: WO2009/145815
PCT Pub. Date: Dec. 3, 2009

(65) Prior Publication Data
US 2011/0028343 A1  Feb. 3, 2011

Related U.S. Application Data

(60) Provisional application No. 61/064,894, filed on Apr. 1, 2008.

(51) Int. Cl.
*G01N 33/53* (2006.01)
(52) U.S. Cl.
USPC ........................................... 435/7.1
(58) Field of Classification Search
None
See application file for complete search history.

(56) References Cited

U.S. PATENT DOCUMENTS

| | | | |
|---|---|---|---|
| 4,921,790 A | 5/1990 | O'Brien | |
| 6,943,235 B1 | 9/2005 | Afar et al. | |
| 6,972,170 B1 | 12/2005 | Cordon-Cardo et al. | |
| 7,244,827 B2 | 7/2007 | Raitano et al. | |
| 7,270,960 B2 | 9/2007 | Hellstrom et al. | |
| 7,288,383 B2 | 10/2007 | Ye et al. | |
| 7,294,704 B2 | 11/2007 | Simon et al. | |
| 7,407,762 B2 | 8/2008 | Auersperg et al. | |
| 2003/0078399 A1 | 4/2003 | Lloyd et al. | |
| 2003/0087250 A1 | 5/2003 | Monahan et al. | |
| 2003/0143667 A1 | 7/2003 | O'Brien et al. | |
| 2003/0211498 A1 | 11/2003 | Morin et al. | |
| 2005/0009120 A1 | 1/2005 | Mok et al. | |
| 2005/0059013 A1 | 3/2005 | Chan et al. | |
| 2005/0095592 A1 | 5/2005 | Jazaeri et al. | |
| 2006/0019256 A1 | 1/2006 | Clarke et al. | |
| 2006/0165676 A1 | 7/2006 | Bergmann et al. | |
| 2007/0026399 A1 | 2/2007 | Auersperg et al. | |
| 2007/0059712 A1 | 3/2007 | Gish et al. | |
| 2007/0172902 A1 | 7/2007 | Zhang et al. | |
| 2007/0178458 A1 | 8/2007 | O'Brien et al. | |
| 2007/0286865 A1 | 12/2007 | Moore et al. | |
| 2008/0081339 A1 | 4/2008 | Liu et al. | |
| 2008/0178308 A1 | 7/2008 | Afar et al. | |
| 2008/0253963 A1 | 10/2008 | Morin et al. | |
| 2008/0254048 A1 | 10/2008 | Cheek et al. | |
| 2008/0254481 A1 | 10/2008 | Love et al. | |
| 2008/0286199 A1 | 11/2008 | Livingston et al. | |
| 2009/0075305 A1 | 3/2009 | Liu et al. | |
| 2011/0045508 A1 | 2/2011 | Ye et al. | |
| 2012/0295814 A1 | 11/2012 | Cramer et al. | |

FOREIGN PATENT DOCUMENTS

| | | |
|---|---|---|
| WO | WO 00/26666 A2 | 5/2000 |
| WO | WO 03/072752 A2 | 9/2003 |
| WO | WO 2005/024055 A1 | 3/2005 |
| WO | WO 2006/119155 A2 | 11/2006 |
| WO | WO 2008/060363 A2 | 5/2008 |
| WO | WO 2009/099561 A2 | 8/2009 |
| WO | WO 2011/085165 A2 | 7/2011 |
| WO | WO 2012/125805 A2 | 9/2012 |

OTHER PUBLICATIONS

Wiener et al (Gynecologic Oncology, 2003, 88:73-79).*
Tockman et al (Cancer Res., 1992, 52:2711s-2718s).*
Kim et al (Clin Cancer Res, 2003, 9(13): 4782-4791).*
O'Rourke, et al., "Autoantibody signatures as biomarkers to distinguish prostate cancer from benign prostatic hyperplasia in patients with increased serum prostate specific antigen," *Clinica Chimica Acta* 413:561-567 (2012).
Rodriguez, et al., "Casein kinase I epsilon interacts with mitochondrial proteins for the growth and survival of human ovarian cancer cells," *EMBO Mol Med.* 4:1-12 (2012).
International Search Report for PCT/US2009/001776 filed Mar. 20, 2009.
Written Opinion of the International Searching Authority for PCT/US2009/001776 filed Mar. 20, 2009.
International Preliminary Report on Patentability for PCT/US2009/001776 filed Mar. 20, 2009.
Agaylan, et al., "A Highly Sensitive Particle Agglutination Assay for the Detection of P53 Autoantibodies in Patients With Lung Cancer," *Cancer* 110(11):2502-2506 (2007).
Anderson, et al. "The Human Plasma Proteome: History, Character, and Diagnostic Prospects," *Mol. Cell. Proteomics* 1(11):845-867 (2002).

(Continued)

*Primary Examiner* — Sean Aeder
(74) *Attorney, Agent, or Firm* — Law Office of: Michael A. Sanzo, LLC

(57) ABSTRACT

The invention is directed to assays for biomarkers associated with ovarian cancer that can be used diagnostically. It includes glass or plastic plates or slides on which the biomarkers have been immobilized and kits containing these plates or slides.

19 Claims, 1 Drawing Sheet

OTHER PUBLICATIONS

Angelopoulou, et al., "Autoantibodies against the p53 tumor suppressor gene product quantified in cancer patient serum with time-resolved immunofluorometry," *Cancer J.* 6(6):315-321 (Nov.-Dec. 1993).
Anim, et al., "Characterisation of inflammatory cells in benign prostatic hyperplasia," *Acta. Histochem.* 100(4):439-449 (1998).
Ashton, et al., "The Association of the COMT V158M Polymorphism with Endometrial/Ovarian Cancer in HNPCC Families Adhering to the Amsterdam Criteria," *Hereditary Cancer in Clinical Practice* 4(2):94-102 (2006).
Bartling, et al., "Comparative application of antibody and gene array for expression profiling in human squamous cell lung carcinoma," *Lung Cancer* 49:145-154 (2005).
"BD Clontech Antibody (AB) Microarray 500" In: "Product overview" 2004. Clontech Laboratories Inc., Mountain View CA 94043 USA; XP002569005.
Boccarelli, et al., "Differential processing of antitumor-active and antitumor-inactive trans platinum compounds by SKOV-3 ovarian cancer cells," *Biochem. Pharm.* 72(3):280-292 (Jul. 2006).
Bouwman, et al., "Microarrays of tumor cell derived proteins uncover a distinct pattern of prostate cancer serum immunoreactivity," *Proteomics* 3:2200-2207 (2003).
Bradford, et al., "Cancer immunomics: Using autoantibody signatures in the early detection of prostate cancer," *Urologic Oncol. Sem. Orig. Invest.* 24:237-242 (2006).
Brawer, et al., "Prostate-Specific Antigen: Current Status," *CA Cancer J. Clin.* 49(5):264-281 (1999).
Di Silverio, et al., "Distribution of Inflammation, Pre-Malignant Lesions, Incidental Carcinoma in Histologically Confirmed Benign Prostatic Hyperplasia: A Retrospective Analysis," *Eur. Urol.* 43(2):164-175 (2003).
Ehrlich, et al., "The reverse capture autoantibody microarray: a native antigen-based platform for autoantibody profiling," *Nat. Protocols* 1(1):452-460 (2006).
Fong, et al., "Natural history and clinical predictors of clinical progression in benign prostatic hyperplasia," *Curr. Opin. Urol.* 15:35-38 (2005).
Fossa, et al., "Serological cloning of cancer/testis antigens expressed in prostate cancer using cDNA phage surface display," *Cancer Immunol. Immunother.* 53:431-438 (2004).
Koziol, et al., "Recursive Partitioning as an Approach to Selection of Immune Markers for Tumor Diagnosis," *Clinical Cancer Research* 9:5120-5126 (Nov. 2003).
Lang, et al., "p53 autoantibodies in patients with urological tumors," *Br. J. Urol.* 82(5):721-726 (1998).
Lee, et al., "Immunomic analysis of human sarcoma," *Proc. Natl. Acad. Sci. USA* 100(5):2651-2656 (Mar. 2003).
Liang, et al., "Anti-5α-Reductase Autoantibodies in the Serum of Patients with Prostatic Cancer," *J. Clin. Endocrinol. Metab.* 71(6):1666-1668 (1990).
Liu, et al., "Proteomics approaches to urologic diseases," *Expert Rev. Proteomics* 3(3):283-296 (2006).
Luo, et al., "Human Prostate Cancer and Benign Prostatic Hyperplasia: Molecular Dissection by Gene Expression Profiling," *Cancer Res.* 61(12):4683-4688 (Jun. 2001).
Luo, et al., "Gene Expression Signature of Benign Prostatic Hyperplasia Revealed by cDNA Microarray Analysis," *Prostate* 51(3):189-200 (2002).
Mahapokai, et al., "Immune response in hormonally-induced prostatic hyperplasia in the dog," *Vet. Immunol. Immunopathol.* 78(3-4):297-303 (2001).
Maxwell, et al., "Novel *PEX1* Coding Mutations and 5' UTR Regulatory Polymorphisms," *Human Mutation* 26(3):279; pp. 1-8 (Sep. 2005).
McAndrew, et al., "Development of a panel of biomarkers for the diagnosis of prostate cancer," AACR Meeting Sep. 27-30, 2010, Denver Colorado, Poster Session A.
McConnell, et al., "The Long-Term Effect of Doxazosin, Finasteride, and Combination Therapy on the Clinical Progression of Benign Prostatic Hyperplasia," *N. Engl. J. Med.* 349(25):2387-2398 (Dec. 2003).

Miller, et al., "Antibody microarray profiling of human prostate cancer sera: Antibody screening and identification of potential biomarkers," *Proteomics* 3:56-63 (2003).
Mintz, et al., "Fingerprinting the circulating repertoire of antibodies from cancer patients," *Nat. Biotechnol.* 21:57-63 (Jan. 2003).
Nickel, et al., "Asymptomatic inflammation and/or infection in benign prostatic hyperplasia," *B. J. Urol.* 84(9):976-981 (1999).
Nilsson, et al., "Autoantibodies to Prostasomes as New Markers for Prostate Cancer," *Ups. J. Med. Sci.* 106(1): 43-49 (2001).
Peiro, et al., "CAS (Cellular Apoptosis Susceptability) Gene Expression in Ovarian Carcinoma," *American Journal of Clinical Pathology* 118(6):922-929 (2002).
Prakash, et al., Symptomatic and asymptomatic benign prostatic hyperplasia: molecular differentiation by using microarrays, *Proc. Nat'l. Acad. Sci. USA* 99(11):7598-7603 (May 2002).
Qin, et al., "Development of a reverse capture autoantibody microarray for studies of antigen-autoantibody profiling," *Proteomics* 6:3199-3209 (2006).
Qiu, et al., "Development of Natural Protein Microarrays for Diagnosing Cancer Based on an Antibody Response to Tumor Antigens," *Proteome Res.* 3(2): 261-267 (2004).
Roessler, et al., "Identification of PSME3 as a Novel Serum Tumor Marker for Colorectal Cancer by Combining Two-dimensional Polyacrylamide Gel Electrophoresis with a Strictly Mass Spectrometry-based Approach for Data Analysis," *Mol. Cell. Prot.* 5(11):2092-2101 (2006).
Roessler, et al., "Identification of Nicotinamide *N*-Methyltransferase as a Novel Serum Tumor Marker for Colorectal Cancer," *Clin. Can. Res.* 11(18):6550-6557 (Sep. 2005).
Segawa, et al., "Measurement and evaluation of serum anti-p53 antibody levels in patients with lung cancer as its initial presentation: a prospective study," *Br J Cancer* 78(5):667-72 (1998).
Song, et al., "Annexin XI Is Associated with Cisplatin Resistance and Related to Tumor Recurrence in Ovarian Cancer Patients," *Clin. Cancr Res.* 13(22):6842-6849 (Nov. 2007).
Soussi, et al., "p53 Antibodies in the Sera of Patients with Various Types of Cancer: A Review," *Cancer Res.* 60:1777-1788 (Apr. 2000).
Stoll, et al., "Microarray technology: an increasing variety of screening tools for proteomic research," *Drug Discovery Today: Targets* 3(I):24-31 (Feb. 2004); XP002569004.
Tan, et al., "Autoantibodies as reporters identifying aberrant cellular mechanisms in tumorigenesis," *J.Clin. Invest.* 108:1411-1415 (Nov. 2001).
Tang, et al., "Autoantibody profiling to identify biomarkers of key pathogenic pathways in mucinous ovarian cancer," *European Journal of Cancer* 46:170-179 (2010).
Tramontano, et al., "Conformation and Glycosylation of a Megalin Fragment Correlate with Nephritogenicity in Heymann Nephritis," *J. Immunol.* 172:2367-2373 (2004).
Turhan, et al., "Adenosquamous Carcinoma of the Prostate," *Int. Urol. Nephrol.* 31(1):89-93 (1999).
UniProtKB/Swiss-Prot database entry O43933 for PEX-1, sequence last modified Jun. 1, 1998.
Wanders, "Metabolic and Molecular Basis of Peroxisomal Disorders: A Review," *Am. J. Med. Genet.* 126A:355-375 (2004).
Wang, et al., "Autoantibody Signatures in Prostate Cancer," *N. Engl. J. Med.* 353(12):1224-1235 (Sep. 2005).
Wiener, et al. "Activated Src protein tyrosine kinase is overexpressed in late-stage human ovarian cancers," *Gynecologic Oncology* 88(1):73-79 (Jan. 2003).
Xu, et al., "Screening of the metastasis-associated genes by gene chip in high metastatic human ovarian cancer cell lines," *Journal of Genetics and Genomics* 34(7):581-590 (Jul. 2007).
Yan, et al., "Rapid and sensitive immunomagnetic-electrochemiluminescent detection of p53 antibodies in human serum," *J Immunol Methods* 288:47-54 (2004).
Yazan, et al., "Proteomic Analysis of Waldenstrom Macroglobulinemia (WM) Using Nanoscale Protein Microarray Techniques," *Blood* 106:Abstract 504 (2005).
Zha, et al., "Peroxisomal Branched Chain Fatty Acid β-Oxidation Pathway Is Upregulated in Prostate Cancer," *The Prostate* 63:316-323 (2005).

Zhang, et al., "Enhancement of Antibody Detection in Cancer Using Panel of Recombinant Tumor-associated Antigens," *Cancer Epidemiology, Biomarkers and Prevention* 12(2):136-143 (Feb. 2003).

Zhang, et al., "Tumor-associated antigen arrays to enhance antibody detection for cancer diagnosis," *Cancer Detect. Prev.* 28:114-118 (2004).

Zhou, et al., "Serological Cloning of PARIS-1: A New TBC Domain-Containing, Immunogenic Tumor Antigen from a Prostate Cancer Cell Line," *Biochem. Biophys. Res. Commun.* 290:830-838 (2002).

Zolg, et al., "How Industry Is Approaching the Search for New Diagnostic Markers and Biomarkers," *Mol. Cell. Prot.* 3:345-354 (2004).

GenBank Accession No. AAL65133; ovarian cancer related tumor marker CA125 [*Homo sapiens*].

Badgwell, et al., "Urinary mesothelin provides greater sensitivity for early stage ovarian cancer than serum mesothelin, urinary hCG free beta subunit and urinary hCG beta core fragment," *Gynecologic Oncology* 106:490-497 (2007).

Chambers, et al., "Ovarian Cancer Biomarkers in Urine," *Clin. Cancer Res.* 12(2):323-327 (Jan. 2006).

Drapkin, et al., "Human Epididymis Protein 4 (HE4) Is a Secreted Glycoprotein that Is Overexpressed by Serous and Endometrioid Ovarian Carcinomas," *Cancer Res.* 65(6):2162-2169 (Mar. 2005).

Gagnon, et al., "Discovery and application of protein biomarkers for ovarian cancer," *Curr. Opin. Obstet. Gynecol.* 20:9-13 (2008).

Gagnon, et al., "Use of a Combination of Approaches to Identify and Validate Relevant Tumor-Associated Antigens and Their Corresponding Autoantibodies in Ovarian Cancer Patients," *Clin. Cancer Res.* 14(3):764-771 (2008).

Geho, et al., "Nanoparticles: potential biomarker harvesters," *Curr. Opin. Chem Biol.* 10(1):56-61 (2006).

Georganopoulou, et al., "Nanoparticle-based detection in cerebral spinal fluid of a soluble pathogenic biomarker for Alzheimer's disease," *PNAS* 102(7):2273-2276 (Feb. 2005).

Hellström, et al., "The HE4 (WFDC2) Protein Is a Biomarker for Ovarian Carcinoma," *Cancer Res.* 63:3695-3700 (Jul. 2003).

Hellström, et al., "SMRP and HE4 as Biomarkers for Ovarian Carcinoma When Used Alone and in Combination with CA125 and/or Each Other," *Adv. Exp. Med. Biol.* 622:15-21 (2008).

Jain, "Nanotechnology in clinical laboratory diagnostics," *Clinica Chimica Acta* 358:37-54 (2005).

Lowe, et al., "Effects of Personal Characteristics on Serum CA125, Mesothelin, and HE4 Levels in Healthy Postmenopausal Women at High-Risk for Ovarian Cancer," *Cancer Epidetniol Biomarkers Prev* 17(9):2480-2487 (Sep. 2008).

Moore, et al., "The use of multiple novel tumor biomarkers for the detection of ovarian carcinoma in patients with a pelvic mass," *Gynecologic Oncology* 108:402-408 (2008).

Moore, et al., "A novel multiple marker bioassay utilizing HE4 and CA125 for the prediction of ovarian cancer in patients with a pelvic mass," *Gynecologic Oncology* 112:40-46 (2009).

O'Brien, et al., "The CA 125 Gene: An Extracellular Superstructure Dominated by Repeat Sequences," *Tumor Biol* 22:348-366 (2001).

Pisitkun, et al., "Discovery of Urinary Biomarkers," *Mol. Cell. Proteomics* 5:1760-1771 (2006).

Roy, et al., "ADAM 12 Cleaves Extracellular Matrix Proteins and Correlates with Cancer Status and Stage," *J. Biol. Chem.* 279(49):51323-51330 (2004).

Schaner, et al., "Gene Expression Patterns in Ovarian Carcinomas," *Mol. Biol. Cell* 14:4376-4386 (Nov. 2003).

Scholler, et al., "Use of Yeast-Secreted In vivo Biotinylated Recombinant Antibodies (Biobodies) in Bead-Based ELISA," *Clin. Cancer Res.* 14(9):2647-2655 (May 2008).

Scholler, et al., "Bead-Based ELISA for Validation of Ovarian Cancer Early Detection Markers," *Clin. Cancer Res.* 12(7):2117-2124 (Apr. 2006).

Schummer, et al., "Comparative hybridization of an array of 21 500 ovarian cDNAs for the discovery of genes overexpressed in ovarian carcinomas," *Gene* 238:375-385 (1999).

Shenoy, et al., "Surface functionalization of gold nanoparticles using hetero-bifunctional poly(ethylene glycol) spacer for intracellular tracking and delivery," *Int. J. Nanomedicine* 1(1):51-57 (2006).

Tantipaiboonwong, et al., "Different techniques for urinary protein analysis of normal and lung cancer patients," *Proteomics* 5:1140-1149 (2005).

Tay, et al., "Correlation of Serum, Urinary and Salivary CA 125 Levels in Patients with Adnexal Masses," *Ann. Acad. Med. Singapore* 23(3):311-314 (1994).

Terry, et al., "Blood and urine markers for ovarian cancer: A comprehensive review," *Disease Markers* 20:53-70 (2004).

Wang, et al., "Gold Nanoparticle-Assisted Protein Enrichment and Electroclution for Biological Samples Containing Low Protein Concentration—A Prelude of Gel Electrophoresis," *J. Proteome Res.* 5(6):1488-1492 (2006).

Ye, et al., "Recent technical strategies to identify diagnostic biomarkers for ovarian cancer," *Expert Rev. Proteomics* 4(1):121-131 (2007).

Ye, et al., "Proteomic-Based Discovery and Characterization of Glycosylated Eosinophil-Derived Neurotoxin and COOH-Terminal Osteopontin Fragments for Ovarian Cancer in Urine," *Clin. Cancer Res.* 12(2):432-441 (Jan. 2006).

Ye, et al., "Haptoglobin-α Subunit As Potential Serum Biomarker in Ovarian Cancer: Identification and Characterization Using Proteomic Profiling and Mass Spectrometry," *Clin. Cancer Res.* 9:2904-2911 (Aug. 2003).

Yin, et al., "Molecular Cloning of the CA125 Ovarian Cancer Antigen," *J. Biol. Chem.* 276(29):27371-27375 (Jul. 2001).

Taylor, et al., "Patient-derived tumor-reactive antibodies as diagnostic markers for ovarian cancer," *Gynecologic Oncology* 115:112-120 (2009).

Cramer, et al., "CA125 Immune Complexes in Ovarian Cancer Patients with Low CA125 Concentrations," *Clin. Chem.* 56(12):1889-1892 (2010).

Cramer, et al., "Conditions Associated with Antibodies Against the Tumor-Associated Antigen MUC1 and Their Relationship to Risk for Ovarian Cancer," *Cancer Epidemiology, Biomarkers & Prevention* 14:1125-1131 (2005).

Ehrlich, et al., "A native antigen "reverse capture" microarray platform for autoantibody profiling of prostate cancer sera," *Proteomics Clin. Appl.* 1(5):476-485 (2007).

Finn, "Immune Response as a Biomarker for Cancer Detection and a Lot More," *N. Engl. J. Med.* 353(12):1288-1290 (Sep. 2005).

Kalia, et al., "General Method for Site-Specific Protein Immobilization by Staudinger Ligation," *Bioconjugate Chem.* 18(4):1064-1069 (2007).

Ries, et al., SEER Cancer Stat. Rev. 1973-1995 National Cancer Institute, Bethesda, MD, (1998); Tables XX-1 through XX-9; Figures XX-1, XX-2 and XX-3.

Rusmini, et al., "Protein Immobilization Strategies for Protein Biochips," *Biomacromolecules* 8:1775-1789 (2007).

Tang, et al., "Autoantibody biomarker profiling for mucinous ovarian cancers," Poster 99th AACR Annual Meeting, Apr. 12-16, 2008; Abstract #4450.

Wilson, et al., "Functional protein microarrays," *Curr. Opin. Chem. Biol.* 6(1):81-85 (2001).

Zhu, et al., "Protein chip technology," *Curr. Opin. Chem. Biol.* 7(1):55-63 (2003).

Halila, et al., "Tumor-associated trypsin inhibitor (TATI) in human ovarian cyst fluid," *Br. J. Cancer* 56(2):153-156 (Aug. 1987).

Timms, et al., "Early Detection of Ovarian Cancer in Samples Pre-Diagnosis Using CA125 and MALDI-MS Peaks," *Cancer Genomics & Proteomics* 8:289-306 (2011).

* cited by examiner

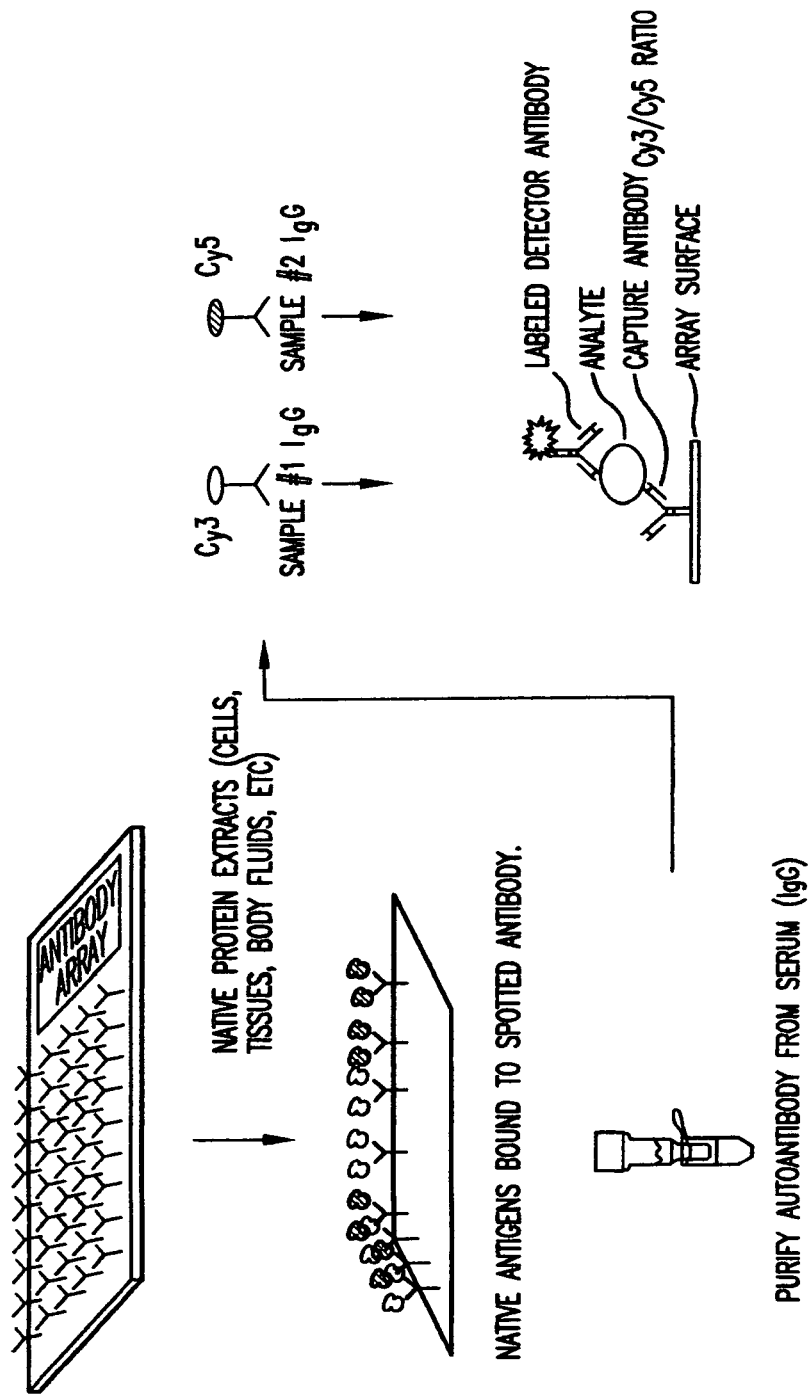

BIOMARKERS OF OVARIAN CANCER

CROSS REFERENCE TO RELATED APPLICATIONS

The present application is US national stage of international application PCT/US2009/001776, which had an international filing date of Mar. 20, 2009, and claims priority to, and the benefit of, United States provisional application 61/064,894 filed on Apr. 1, 2008 incorporated herein by reference in its entirety. The international application was published in English under PCT Article 21(2) on Dec. 3, 2009.

FIELD OF THE INVENTION

The present invention is directed to biomarkers that can be used in the diagnosis of ovarian cancer. The invention also includes assays in which the biomarkers are immobilized on plates or slides by monoclonal antibodies and then used in determining the antibody profile of a subject.

BACKGROUND OF THE INVENTION

Ovarian cancer is the fifth leading cause of death from cancer in U.S. women. In most instances, a diagnosis is not made until the cancer is in an advanced state; at a time when the five-year survival rate of patients is only about 28% (Ries, et al., SEERC Cancer Stat. Rev. 1973-1995 (1998)). In contrast, the five year survival rate for women diagnosed with localized disease is about 95%. These statistics provide an incentive to search for tests that can be used to identify ovarian cancer at an early stage.

Proteins preferentially expressed by ovarian cancer cells but not by normal cells may elicit a host immune response that will be reflected in the antibodies present in a host. For example, Zheng et al. demonstrated the presence of serum autoantibodies to a panel of known antigens in various human cancers (Zhang, et al., *Cancer Epidemiol Biomarkers Prev.* 12:136-143 (2003); Zhang, *Cancer Detect. Prev.* 28(2):114-118 (2004)). The results strongly suggest that uniquely constituted antigen panels or protein microarrays may provide an approach for discriminating autoantibody reactivity between cancer patients and control individuals.

One disadvantage with many assays that look at the array of antibodies present in a patient is that they use antigens that are denatured due to having been directly bound to a microtiter plate and which lack posttranslational modifications due to their having been either chemically synthesized or recombinantly produced in bacteria. As a result, the ability of antibodies to recognize and bind antigens is impaired and a distorted profile is obtained. Recently, an improved assay has been developed in which antigens are bound to a plate or slide by a monoclonal antibody (WO 2006/119155; Qin, et al., *Proteomics* 6:3199-209 (2006)). This preserves the normal conformation of the antigens. In addition, the antigens are derived from native cells rather than being synthesized or recombinantly produced in bacteria. Thus, they also retain posttranslational modifications that may affect the binding of antibodies. Once an appropriately prepared plate is available, it is used to compare the binding of antibodies from patients with a particular disease or condition with those derived from subjects known to be disease free. In this manner, it is possible to identify a set of antigenic differences that are characteristic of a disease and that have the potential of being used diagnostically.

SUMMARY OF THE INVENTION

General Summary

Previous reports have described in detail a microarray assay for examining the antibody profile of a sample of blood, plasma or serum (WO 2006/119155; Qin, et al., *Proteomics* 6:3199-209 (2006); Ehrlich, et al., *Nat. Protocols* 1:452-60 (2006); Liu, et al., *Expert Rev. Proteomics* 3:283-96 (2006), all incorporated herein by reference in their entirety). The main characteristic of this assay is that monoclonal antibodies, each recognizing a single known antigen, are bound to a solid support, such as a glass slide, with each antibody at a separate location. The corresponding antigens are then bound to the immobilized monoclonal antibodies, e.g., by incubating a crude cell lysate with the prepared support. In this way, a microarray is formed in which antigens maintaining their native structural characteristics are immobilized, each antigen at a unique site on the assay support.

In the next step, the IgG fraction is isolated from a "test sample" of blood, plasma or serum and the "test antibodies" thus obtained are detectably labeled with a fluorescent dye. These labeled antibodies are then combined with an equal amount of "control antibodies" that have been isolated from a second sample of blood, serum or plasma (e.g., from a subject known to be disease free). The control antibodies are attached to a second fluorescent label that is different than, and distinguishable from, the label used for the test antibodies. The mixture of labeled test and control antibodies is incubated with the immobilized antigens and the relative amount of binding is determined based upon the detectable labels. The assay procedure can be used to compare the antibodies present in patients having a disease such as cancer to the antibodies in samples from normal individuals. Results have indicated that the procedure can be used to identify antigens that are characteristic of, inter alia, prostate cancer (see WO 2006/119155).

Applying the assay described above to patients with ovarian cancer, a set of antigenic markers have been identified that are consistently altered in patients with this disease and which may be used diagnostically. Some of these biomarkers are elevated in ovarian cancer patients relative to normal controls whereas others are decreased. The biomarkers are shown in Tables 1-3 along with its UniProt Knowledgebase accession number. Each accession number is associated with a unique amino acid sequence that unambiguously defines the protein and which is readily accessible to the public. It will be understood that, for the purposes of the present application, reference to a particular biomarker in Tables 1-3 means the marker defined by the accession number provided.

Most of the markers do not appear to have been previously associated with ovarian cancer. Assays for these markers (e.g., ELISA assays or radioimmunoassays) can be used on samples derived from patients that have symptoms suggesting that they may have ovarian cancer to help make a diagnosis. Alternatively a multiplex platform consisting of 5 or more selected antigens could be used in an antibody profiling assay. Assays may also be used on patients already known to have ovarian cancer to assess whether the disease is progressing and whether it is responding to therapy. The markers shown in Tables 2 and 3 are associated with specific subgroups of ovarian cancer patients. The markers shown in Table 2 are altered in patients with mucinous ovarian cancer but not in patients with serous ovarian cancer. The markers in Table 3 are decreased in mucinous ovarian cancer patients that smoke relative to mucinous ovarian cancer patients that do not smoke.

A few of the cancer associated markers (CAMs) identified appear to have been previously implicated in ovarian cancer. These include: topoisomerase II alpha; c-src tyrosine kinase; catechol-O-methyltransferase; nuclear receptor coactivator 3; NM23; and cyclin-dependent kinase 4. However, it does not appear that autoantibody assays of the type discussed herein have been used to evaluate these markers in the past. Since antibodies to markers will be amplified as the result of natural immunological processes, these assays are, in effect, increased in sensitivity. In addition, the IgG fraction can be precipitated from serum using routine techniques and this reduces the likelihood of distorted assay results due to other serum components.

Detailed Summary

In its first aspect, the invention is directed to a method of diagnostically evaluating a subject for ovarian cancer by obtaining a "test" biological sample from the subject and assaying the sample for one or more of the following cancer associated markers (CAMs): CSE1 chromosome segregation 1-like (yeast) (UniProt Knowledgebase sequence P55060); casein kinase 1, epsilon (UniProt Knowledgebase sequence P49674); v-crk sarcoma virus CT 10 oncogene homolog (avian) UniProt Knowledgebase sequence P46108); WAS protein family, member 1 (UniProt Knowledgebase sequence Q92558); erythrocyte membrane protein band 4.9 (dematin) (UniProt Knowledgebase sequence Q08495); potassium large conductance calcium-activated channel, subfamily M, alpha member 1 (UniProt Knowledgebase sequence Q12791); nuclear receptor coactivator 3 (UniProt Knowledgebase sequence Q9Y6Q9); TEA domain family member 1 (SV40 transcriptional enhancer factor) (UniProt Knowledgebase sequence P28347); peroxisome biogenesis factor 1 (UniProt Knowledgebase sequence O43933); translin-associated factor X (UniProt Knowledgebase sequence Q99598); G protein-coupled receptor 51 (UniProt Knowledgebase sequence O75899); solute carrier family 9 (sodium/hydrogen exchanger), isoform 1 (antiporter, $NA^+/H^+$, amiloride sensitive) (UniProt Knowledgebase sequence P19634); integrin, alpha 2 (CD49B, alpha 2 subunit of VLA-2 receptor) (UniProt Knowledgebase sequence P17301); MCM6 minichromosome maintenance deficient 6 (MIS5 homolog, S. pombe) (S. cerevisiae) (UniProt Knowledgebase sequence Q14566); syntaxin 6 (UniProt Knowledgebase sequence O43752); KH domain containing, RNA binding, signal transduction associated 1 (UniProt Knowledgebase sequence Q07666); dystrophia myotonica-protein kinase (UniProt Knowledgebase sequence Q09013); eukaryotic translation initiation factor 4 gamma, 1 (UniProt Knowledgebase sequence Q04637); Rho GDP dissociation inhibitor (GDI) beta (UniProt Knowledgebase sequence P52566); endothelin receptor type A (UniProt Knowledgebase sequence P25101); synaptophysin (UniProt Knowledgebase sequence P08247); transcription factor 3 (E2A immunoglobulin enhancer binding factors E12/E47) (UniProt Knowledgebase sequence P15923); fibronectin 1 (UniProt Knowledgebase sequence P02751); RAS p21 protein activator (GTPase activating protein) 1 (UniProt Knowledgebase sequence P20936); SWI/SNF related, matrix associated, actin dependent regulator of chromatin, subfamily a, member 2 (UniProt Knowledgebase sequence P51531); syntaxin binding protein 5 (tomosyn) (UniProt Knowledgebase sequence Q5T5C0); Ras-GTPase-activating protein SH3-domain-binding protein (UniProt Knowledgebase sequence Q13283); glutamate receptor, ionotropic, N-methyl D-aspartate 2B (UniProt Knowledgebase sequence Q13224); zeta-chain (TCR) associated protein kinase 70 kDa (UniProt Knowledgebase sequence P43403); TATA box binding protein (UniProt Knowledgebase sequence P20226). The results from the test biological sample are compared to those from one or more similar "control samples" obtained from subjects known to be disease free or from the general population. If the comparison indicates that the test sample has a higher amount of one or more CAMs, this is an indication that the test subject has ovarian cancer. As the number of elevated CAMs increases, so does the probability that ovarian cancer is present and progressing.

The term "diagnostically evaluating a subject for ovarian cancer" means that a sample from the subject is tested to determine if it has the abnormalities described herein as being characteristic of samples derived from ovarian cancer patients. As discussed above, the abnormalities may be an indication that a woman not previously diagnosed as having ovarian cancer does, in fact, have the disease. However, it will be understood that these assays may be used in other contexts as well. For example, they may be used to determine whether a patient with a disease in remission is having a relapse or whether a treatment regimen is effective in returning a patient to a more normal profile. In cases where, a patient shows an elevation in only one, or a few markers, and further examination fails to reveal overt ovarian disease, the patient should be followed closely to see if abnormalities in additional CAMs develop and whether ovarian tumors become detectable.

In addition to assays for CAMs that are elevated in samples derived from patients with ovarian cancer, the invention is directed to diagnostic assays for CAMs that have been found to be characteristically lower in ovarian cancer patients. Thus, in another aspect, the invention is directed to a method of diagnostically evaluating a subject using essentially the procedure described above but in which disease presence or progression is indicated by one or more CAMs in test biological samples being lower than in the control samples. CAMs characteristically reduced are: synapsin II (UniProt Knowledgebase sequence Q92777); sortilin-related receptor, L (DLR class) A repeats-containing (UniProt Knowledgebase sequence Q92673); excision repair cross-complementing rodent repair deficiency, complementation group 2 (xeroderma pigmentosum D) (UniProt Knowledgebase sequence P18074); signal transducer and activator of transcription 6, interleukin-4 induced (UniProt Knowledgebase sequence P42226); tripartite motif-containing 3 (UniProt Knowledgebase sequence O75382); protein kinase C, theta (UniProt Knowledgebase sequence Q04759); syntaxin 8 (UniProt Knowledgebase sequence Q9UNK0); glutamate-ammonia ligase (glutamine synthase) (UniProt Knowledgebase sequence P15104); protein kinase C, beta 1(UniProt Knowledgebase sequence P05771); chromosome condensation 1(UniProt Knowledgebase sequence P18754); DEAH (Asp-Glu-Ala-His) box polypeptide 16 (UniProt Knowledgebase sequence O60231); ribosomal protein L22 (UniProt Knowledgebase sequence P35268); caveolin 1, caveolae protein, 22 kDa (UniProt Knowledgebase sequence Q03135); retinoblastoma-like 2 (p130) (UniProt Knowledgebase sequence Q08999); cyclin-dependent kinase inhibitor 1A (p21, Cip1) (UniProt Knowledgebase sequence P38936); protein tyrosine phosphatase, receptor-type, Z polypeptide 1 (UniProt Knowledgebase sequence O76043); general transcription factor II, i (UniProt Knowledgebase sequence O15359); adaptor-related protein complex 2, alpha 1 subunit (UniProt Knowledgebase sequence O95782); linker for activation of T cells (UniProt Knowledgebase sequence O43561); thyroid autoantigen 70 kDa (Ku antigen) (UniProt Knowledgebase sequence P12956); 5-hydroxytryptamine (serotonin) receptor 2A (UniProt Knowledgebase sequence P28223).

As recognized in the art the amount of CAM present in normal individuals will typically be expressed as a range. The amount of a CAM in a test biological sample is "higher than" or "lower than" the control amount if it falls outside of this range, with greater variation more strongly suggesting disease presence. For example if a CAM was found to be present in serum at 20±6 ug/ml in normal subjects, an assay indicating a concentration of 25 ug/ml would not be indicative of disease presence, whereas a concentration of 40 ug/ml would be considered high and, depending on the CAM, may be an indication of cancer. A concentration of 80 ug/ml would be even more suggestive.

Examples of test biological samples that can be used include blood, plasma, serum, urine, and ovarian fluid (i.e., fluid immediately surrounding the ovary). The most preferred of these is blood, plasma or serum. The amount of CAM present in the biological sample can be determined by any method known in the art, e.g. by ELISA, radioimmunoassay or radioreceptor assay. The most preferred method however is by an antibody profiling assay. For the purposes of the present application, this is defined as assessing the amount CAM present indirectly by examining the amount of antibody against the CAM in the biological sample. Specific examples are provided herein and are described in WO 2006/119155 (incorporated herein by reference in its entirety). Preferably at least 7 different CAMs should be examined and more preferably, 20, 40 or all CAMs.

Certain of the CAMs are characteristic not only of the presence of ovarian cancer but also of a particular type of cancer. For example, mucinous (as opposed to serous) ovarian cancer is suggested by increased levels of one or more of the following markers: non-metastatic cells 1, protein (NM23) (UniProt Knowledgebase sequence P15531); zeta-chain (TCR) associated protein kinase 70 kDa (UniProt Knowledgebase sequence P43403); TATA box binding protein (UniProt Knowledgebase sequence P20226); and/or a decreased level of one or more of: thyroid autoantigen 70 kDa (Ku antigen) (UniProt Knowledgebase sequence P12956); and 5-hydroxytryptamine (serotonin) receptor 2A (UniProt Knowledgebase sequence P28223). In addition, there are certain CAMs that are found to be decreased in mucinous cancer patients that smoke relative to nonsmoking patients. These CAMs are: survival of motor neuron protein interacting protein 1 (UniProt Knowledgebase sequence O14893); three prime repair exonuclease 1 (UniProt Knowledgebase sequence Q9BPW1); chromogranin B (secretogranin 1) (UniProt Knowledgebase sequence P05060); solute carrier family 25 (mitochondrial carrier, Aralar), member 12 (UniProt Knowledgebase sequence O75746); cyclin-dependent kinase 4 (UniProt Knowledgebase sequence P11802); and likely ortholog of rat F-actin binding protein nexilin (UniProt Knowledgebase sequence Q0ZGT2).

In another aspect, the invention includes a solid support (e.g. a glass or plastic plate or slide) having at least 7 different CAMs, each attached at a different position. The CAMs are selected from: CSE1 chromosome segregation 1-like (yeast) (UniProt Knowledgebase sequence P55060); casein kinase 1, epsilon (UniProt Knowledgebase sequence P49674); v-crk sarcoma virus CT10 oncogene homolog (avian) UniProt Knowledgebase sequence P46108); topoisomerase (DNA) II alpha 170 kDa (UniProt Knowledgebase sequence P11388); c-src tyrosine kinase (UniProt Knowledgebase sequence P41240); catechol-O-methyltransferase (UniProt Knowledgebase sequence P21964); WAS protein family, member 1 (UniProt Knowledgebase sequence Q92558); erythrocyte membrane protein band 4.9 (dematin) (UniProt Knowledgebase sequence Q08495); potassium large conductance calcium-activated channel, subfamily M, alpha member 1 (UniProt Knowledgebase sequence Q12791); nuclear receptor coactivator 3 (UniProt Knowledgebase sequence Q9Y6Q9); TEA domain family member 1 (SV40 transcriptional enhancer factor) (UniProt Knowledgebase sequence P28347); peroxisome biogenesis factor 1 (UniProt Knowledgebase sequence O43933); translin-associated factor X (UniProt Knowledgebase sequence Q99598); G protein-coupled receptor 51 (UniProt Knowledgebase sequence O75899); solute carrier family 9 (sodium/hydrogen exchanger), isoform 1 (antiporter, $NA^+/H^+$, amiloride sensitive) (UniProt Knowledgebase sequence P19634); integrin, alpha 2 (CD49B, alpha 2 subunit of VLA-2 receptor) (UniProt Knowledgebase sequence P17301); MCM6 minichromosome maintenance deficient 6 (MIS5 homolog, S. pombe) (S. cerevisiae) (UniProt Knowledgebase sequence Q14566); syntaxin 6 (UniProt Knowledgebase sequence O43752); KH domain containing, RNA binding, signal transduction associated 1 (UniProt Knowledgebase sequence Q07666); dystrophia myotonica-protein kinase (UniProt Knowledgebase sequence Q09013); eukaryotic translation initiation factor 4 gamma, 1 (UniProt Knowledgebase sequence Q04637); Rho GDP dissociation inhibitor (GDI) beta (UniProt Knowledgebase sequence P52566); endothelin receptor type A (UniProt Knowledgebase sequence P25101); synaptophysin (UniProt Knowledgebase sequence P08247); transcription factor 3 (E2A immunoglobulin enhancer binding factors E12/E47) (UniProt Knowledgebase sequence P15923); fibronectin 1 (UniProt Knowledgebase sequence P02751); RAS p21 protein activator (GTPase activating protein) 1 (UniProt Knowledgebase sequence P20936); SWI/SNF related, matrix associated, actin dependent regulator of chromatin, subfamily a, member 2 (UniProt Knowledgebase sequence P51531); syntaxin binding protein 5 (tomosyn) (UniProt Knowledgebase sequence Q5T5C0); Ras-GTPase-activating protein SH3-domain-binding protein (UniProt Knowledgebase sequence Q13283); glutamate receptor, ionotropic, N-methyl D-aspartate 2B (UniProt Knowledgebase sequence Q13224); synapsin II (UniProt Knowledgebase sequence Q92777); sortilin-related receptor, L (DLR class) A repeats-containing (UniProt Knowledgebase sequence Q92673); excision repair cross-complementing rodent repair deficiency, complementation group 2 (xeroderma pigmentosum D) (UniProt Knowledgebase sequence P18074); signal transducer and activator of transcription 6, interleukin-4 induced (UniProt Knowledgebase sequence P42226); tripartite motif-containing 3 (UniProt Knowledgebase sequence O75382); protein kinase C, theta (UniProt Knowledgebase sequence Q04759); syntaxin 8 (UniProt Knowledgebase sequence Q9UNK0); glutamate-ammonia ligase (glutamine synthase) (UniProt Knowledgebase sequence P15104); protein kinase C, beta 1(UniProt Knowledgebase sequence P05771); chromosome condensation 1(UniProt Knowledgebase sequence P18754); DEAH (Asp-Glu-Ala-His) box polypeptide 16 (UniProt Knowledgebase sequence O60231); ribosomal protein L22 (UniProt Knowledgebase sequence P35268); caveolin 1, caveolae protein, 22 kDa (UniProt Knowledgebase sequence Q03135); retinoblastoma-like 2 (p130) (UniProt Knowledgebase sequence Q08999); cyclin-dependent kinase inhibitor 1A (p21, Cip 1) (UniProt Knowledgebase sequence P38936); protein tyrosine phosphatase, receptor-type, Z polypeptide 1 (UniProt Knowledgebase sequence O76043); general transcription factor II, i (UniProt Knowledgebase sequence O15359); adaptor-related protein complex 2, alpha 1 subunit (UniProt Knowledgebase sequence O95782); linker for activation of T cells (UniProt Knowledgebase sequence O43561); non-metastatic cells 1, protein (NM23) (UniProt Knowledgebase sequence P15531); zeta-chain (TCR) associated protein kinase 70 kDa (UniProt Knowledgebase sequence P43403); TATA box binding protein (UniProt Knowledgebase sequence P20226); thyroid autoantigen 70 kDa (Ku antigen) (UniProt Knowledgebase sequence P12956); 5-hydroxytryptamine (serotonin) receptor 2A (UniProt Knowledgebase sequence P28223); survival of motor neuron protein interacting protein 1 (UniProt Knowledgebase sequence O14893); three prime repair exonuclease 1 (UniProt Knowledgebase sequence Q9BPW1); chromogranin B (secretogranin 1) (UniProt Knowledgebase sequence P05060); solute carrier family 25 (mitochondrial carrier, Aralar), member 12 (UniProt Knowledgebase sequence O75746); cyclin-dependent kinase 4 (UniProt Knowledgebase sequence P11802); likely ortholog of rat F-actin binding protein nexilin (UniProt Knowledgebase sequence Q0ZGT2). Preferably each CAM is attached to the plate or slide by a monoclonal antibody that specifically recognizes it. In a preferred embodiment at least 20 CAMs are attached to the plate or slide, more preferably, at least 40 CAMs and, most preferably, all of the above CAMs. In general, there should not be a total of more than 100 different antigens of any type (and preferably no more than 65, 70 or 75) bound to the solid support. However, if desired, a single type of antigen may be bound to more than one site in order to provide a verification of the accuracy of results. For example, an array may have 30 or 40 different CAMs in triplicate, i.e., bound at three different sites. The array may, if desired, include only the CAMs shown herein and no other antigens, or a few (e.g., 1-5) additional antigens to serve as positive or negative controls, i.e., antigens that would be expected not to change as long as samples were being properly collected and assays properly run. The use of positive and negative controls in this manner is well known in the art.

The plate or slide with attached CAMs may be included as part of a kit along with instructions concerning its use in performing a diagnostic assay for ovarian cancer. Optionally, the kit may also include a control sample derived from one or more individuals known not to have ovarian disease or from the general population and/or other components that may be needed to perform assays such as buffers, fluorescent labeling reagents, antibodies that serve as standards, etc.

The invention also includes an assay for comparing the autoantibodies present in a subject. The assay involves obtaining an immobilized array of CAMs, each CAM being attached to the surface of a solid support by an antibody, especially a monoclonal antibody, that specifically recognizes it. The CAMs are selected from the group consisting of: CSE1 chromosome segregation 1-like (yeast) (UniProt Knowledgebase sequence P55060); casein kinase 1, epsilon (UniProt Knowledgebase sequence P49674); v-crk sarcoma virus CT10 oncogene homolog (avian) UniProt Knowledgebase sequence P46108); topoisomerase (DNA) II alpha 170 kDa (UniProt Knowledgebase sequence P11388); c-src tyrosine kinase (UniProt Knowledgebase sequence P41240); catechol-O-methyltransferase (UniProt Knowledgebase sequence P21964); WAS protein family, member 1 (UniProt Knowledgebase sequence Q92558); erythrocyte membrane protein band 4.9 (dematin) (UniProt Knowledgebase sequence Q08495); potassium large conductance calcium-activated channel, subfamily M, alpha member 1 (UniProt Knowledgebase sequence Q12791); nuclear receptor coactivator 3 (UniProt Knowledgebase sequence Q9Y6Q9); TEA domain family member 1 (SV40 transcriptional enhancer factor) (UniProt Knowledgebase sequence P28347); peroxisome biogenesis factor 1 (UniProt Knowledgebase sequence O43933); translin-associated factor X (UniProt Knowledgebase sequence Q99598); G protein-coupled receptor 51 (UniProt Knowledgebase sequence O75899); solute carrier family 9 (sodium/hydrogen exchanger), isoform 1 (antiporter, $Na^+/H^+$, amiloride sensitive) (UniProt Knowledgebase sequence P19634); integrin, alpha 2 (CD49B, alpha 2 subunit of VLA-2 receptor) (UniProt Knowledgebase sequence P17301); MCM6 minichromosome maintenance deficient 6 (MIS5 homolog, S. pombe) (S. cerevisiae) (UniProt Knowledgebase sequence Q14566); syntaxin 6 (UniProt Knowledgebase sequence O43752); KH domain containing, RNA binding, signal transduction associated 1 (UniProt Knowledgebase sequence Q07666); dystrophia myotonica-protein kinase (UniProt Knowledgebase sequence Q09013); eukaryotic translation initiation factor 4 gamma, 1 (UniProt Knowledgebase sequence Q04637); Rho GDP dissociation inhibitor (GDI) beta (UniProt Knowledgebase sequence P52566); endothelin receptor type A (UniProt Knowledgebase sequence P25101); synaptophysin (UniProt Knowledgebase sequence P08247); transcription factor 3 (E2A immunoglobulin enhancer binding factors E12/E47) (UniProt Knowledgebase sequence P15923); fibronectin 1 (UniProt Knowledgebase sequence P02751); RAS p21 protein activator (GTPase activating protein) 1 (UniProt Knowledgebase sequence P20936); SWI/SNF related, matrix associated, actin dependent regulator of chromatin, subfamily a, member 2 (UniProt Knowledgebase sequence P51531); syntaxin binding protein 5 (tomosyn) (UniProt Knowledgebase sequence Q5T5C0); Ras-GTPase-activating protein SH3-domain-binding protein (UniProt Knowledgebase sequence Q13283); glutamate receptor, ionotropic, N-methyl D-aspartate 2B (UniProt Knowledgebase sequence Q13224); synapsin II (UniProt Knowledgebase sequence Q92777); sortilin-related receptor, L (DLR class) A repeats-containing (UniProt Knowledgebase sequence Q92673); excision repair cross-complementing rodent repair deficiency, complementation group 2 (xeroderma pigmentosum D) (UniProt Knowledgebase sequence P18074); signal transducer and activator of transcription 6, interleukin-4 induced (UniProt Knowledgebase sequence P42226); tripartite motif-containing 3 (UniProt Knowledgebase sequence O75382); protein kinase C, theta (UniProt Knowledgebase sequence Q04759); syntaxin 8 (UniProt Knowledgebase sequence Q9UNK0); glutamate-ammonia ligase (glutamine synthase) (UniProt Knowledgebase sequence P15104); protein kinase C, beta 1(UniProt Knowledgebase sequence P05771); chromosome condensation 1(UniProt Knowledgebase sequence P18754); DEAH (Asp-Glu-Ala-His) box polypeptide 16 (UniProt Knowledgebase sequence O60231); ribosomal protein L22 (UniProt Knowledgebase sequence P35268); caveolin 1, caveolae protein, 22 kDa (UniProt Knowledgebase sequence Q03135); retinoblastoma-like 2 (p130) (UniProt Knowledgebase sequence Q08999); cyclin-dependent kinase inhibitor 1A (p21, Cip 1) (UniProt Knowledgebase sequence P38936); protein tyrosine phosphatase, receptor-type, Z polypeptide 1 (UniProt Knowledgebase sequence O76043); general transcription factor II, i (UniProt Knowledgebase sequence O15359); adaptor-related protein complex 2, alpha 1 subunit (UniProt Knowledgebase sequence O95782); linker for activation of T cells (UniProt Knowledgebase sequence O43561); non-metastatic cells 1, protein (NM23) (UniProt Knowledgebase sequence P15531); zeta-chain (TCR) associated protein kinase 70 kDa (UniProt Knowledgebase sequence P43403); TATA box binding protein (UniProt Knowledgebase sequence P20226); thyroid autoantigen 70 kDa (Ku antigen) (UniProt Knowledgebase sequence P12956); 5-hydroxytryptamine (serotonin) receptor 2A (UniProt Knowledgebase sequence P28223); survival of motor neuron protein interacting protein 1 (UniProt Knowledgebase sequence O14893); three prime repair exonuclease 1 (UniProt Knowledgebase sequence Q9BPW1); chromogranin B (secretogranin 1) (UniProt Knowledgebase sequence P05060); solute carrier family 25 (mitochondrial carrier, Aralar), member 12 (UniProt Knowledgebase sequence O75746); cyclin-dependent kinase 4 (UniProt Knowledgebase sequence P11802); and likely ortholog of rat F-actin binding protein nexilin (UniProt Knowledgebase sequence Q0ZGT2). Test antibodies are then derived from a first sample of blood, serum or plasma and attached to a first detectable label. Control antibodies derived from a second sample of blood, serum or plasma are also obtained and are attached to a second detectable label that can be distinguished from the first detectable label after incubation with the immobilized CAMs. In the next step, the labeled test antibodies and labeled control antibodies are incubated with the array of immobilized CAMs. Unbound labeled antibodies are then removed and the amount of the first and second detectable labels associated with each CAM is determined.

In a preferred embodiment, the first and said second detectable labels are dyes or fluorescent labels chosen so that the first detectable label absorbs or fluoresces at a different wavelength than the second detectable label, e.g., Cy3 and Cy5 fluorescent dyes may be used. Preferably, the test antibodies are from a subject that is known to have, or is suspected of having, ovarian cancer and the control antibodies are from a subject that does not have this disease.

BRIEF DESCRIPTION OF THE DRAWINGS

FIG. 1 represents a schematic of a "reverse capture" microarray assay. Highly specific monoclonal antibodies are spotted on an array surface and antigens from cell extracts are then bound to each. Test and control autoantibodies are then labeled with different CyDyes, and incubated with the array of immobilized antigens. After incubation, the ratio of the fluors present at each site on the array surface reflects the relative abundance of the autoantibodies in the samples.

DETAILED DESCRIPTION OF THE INVENTION

The present invention is based upon the identification of antigens that are altered in subjects with ovarian cancer relative to subjects that do not have ovarian cancer. These antigens are shown in Tables 1-3, are all well known in the art and are unambiguously identified by the UniProt Knowledgebase sequence accession numbers also provided in the Tables. Although a difference in any of these CAMs in a subject is suggestive of the presence of ovarian cancer, a better assessment can be made by examining many, preferably all, of the antigens.

One way of assaying individual markers is to use an ELISA, radioimmuno- or radioreceptor assay. Alternatively, microarray plates can be used to examine multiple antigens at once. The most preferred method of doing this is to immobilize an array of monoclonal antibodies, each recognizing a specific antigen, to an inert solid surface. Many plastic, glass or nylon surfaces are known in the art and can be used for this purpose. Monoclonal antibodies appropriate for attachment are commercially available, e.g., from Clontech Inc. and other manufacturers, and in some cases it may be possible to purchase arrays already attached to a surface. If desired, fragments derived from the monoclonal antibodies that maintain the ability to specifically recognize antigen may also be used.

The next step in the procedure is to attach the antigens to the immobilized antibodies. This may be accomplished by lysing cells derived from culture or in vivo, removing cellular debris and then incubating the crude antigen solution with the array of immobilized antibodies. At the end of the incubation, unattached materials and antigens are removed, thereby leaving behind an array of antigens attached to slides or plates by the immobilized monoclonal antibodies. The identity of each of the attached antigens is known from the specificity of the antibody to which it is attached. In other words, each antibody is at a specific location on the slide or plate and recognizes only one particular type of antigen.

Once the array of immobilized antigens has been prepared, the next step is to prepare the antibody samples that will undergo testing. A sample is removed from a subject being tested for ovarian cancer. A second "control" sample is then obtained from one or more other individuals that do not have the disease. The IgG fraction present in the samples is then isolated using any method known in the art and the resulting antibodies are labeled. Any type of label that can be detected using a microarray assay is compatible with the present invention, with fluorescent dyes such as Cy3 and Cy5 being preferred. The main requirement for labeling is that the label attached to the antibodies derived from the test subject must be distinguishable from those derived from the control subject after binding has occurred. Thus, the absorption or emission wavelengths of the dyes should be sufficiently different to allow them to be readily distinguished.

After test and control antibodies have been labeled, an equal amount of each (e.g., 100 microgram) is placed in a buffer solution and incubated with the array of immobilized antigens. The incubation buffer may consist of any type of standard buffer used in handling antibodies, e.g., PBS. The incubations may be carried out at about room temperature for a period ranging from 15 minutes to 2 hours with about 45 minutes being generally preferred. At the end of this time, unbound labeled antibody is removed and plates or slides are then analyzed to determine the amount of fluorescence or light absorption associated with each immobilized antigen. By comparing the results obtained using wavelengths characteristic of the dye attached to the test antibodies with those characteristic of the dye attached to the control antibodies, a profile can be obtained in which antibodies preferentially present in the test sample are identified. The presence of such antibodies is an indication that the antigens that they recognize are produced to a greater extent in the test subject.

Microarray plates or slides containing an array of the CAMs (or a subset of the CAMs) may be prepared and included as part of a kit. The kit will also include instructions describing how the plates or slides can be used in diagnostic assays for ovarian cancer. In addition, it may include other components needed in assays such as buffers or a "control" preparation of antibodies.

Although the antigens that have been identified herein are characteristic of ovarian cancer, it is expected that some of the antigens, or combinations of antigens will also be useful in diagnosing other types of disease as well. Assays utilizing arrays of the markers in Tables 1-3 may also be combined with assays of other factors of diagnostic value.

EXAMPLES

We have applied an innovative reverse-capture antibody array assay (described in WO 2006/119155), to profile the autoantibodies in eleven mucinous and five serous ovarian cancer plasma samples. Briefly, immunoglobulin G antibodies (IgG) were isolated from patient and normal control plasma samples. Individual patient IgG was labeled with a fluorescent fluor and combined with an equal amount of normal control IgG, which was pooled from a group of 20 healthy female donors and labeled with another color fluorescent fluor. The combined IgGs were then hybridized to an antibody array, which had been precoated with antigens extracted from tumor tissues. After hybridization, the array was washed and scanned by a fluorescence scanner. The intensities of the two-color fluorescent fluors at each antibody spot represented the competitive binding of patient and normal IgGs to the antigen at that spot.

To account for any labeling and binding artifacts, another antibody array hybridization experiment was conducted using the same IgGs but for which the fluor labels for the patient and normal IgGs were reversed. The array data were normalized and analyzed by open-source microarray software MeV 4.0 to identify significant autoantibody biomarkers.

By clustering analysis of the microarray data, we have identified a group of autoantibody biomarkers whose titers were significantly different (up or down) in the plasma samples of cancer patients relative to that of the normal control sample (see Table 1). We also noted that there are some autoantibody biomarkers that are more prominent in plasma of patients with mucinous ovarian cancer (see Table 2). In this regard, it should be noted that mucinous ovarian cancers are clinically and morphologically distinct from other histopathologic subtypes of ovarian cancer. Studies have suggested that patients with mucinous histologic subtypes of tumors respond poorly to standard platinum-taxane chemotherapy. More studies may reveal if these mucinous-specific biomarkers are derived from mucinous tumor-specific pathogenesis pathways.

In addition, epidemiologic studies have shown that smoking is a risk factor for developing mucinous ovarian tumors, with an adjusted odds ratio of smoking exposure to mucinous cancer development ranging from 1.5 to 3.2. By analyzing within the mucinous group, we identified autoantibody biomarkers whose titers in the smoking samples are significantly lower than the titers in nonsmoking samples (see Table 3).

Many of the antigens recognized by these biomarkers are involved in signaling pathways that regulate cytoskeleton remodeling, cell migration, growth and survival of cancer cells, suggesting that elevated plasma autoantibodies from ovarian cancer patients might have heightened reactivities with epitopes presented by these antigens.

TABLE 1

Biomarkers for Ovarian Cancer

| Biomarker | Accession No. | Level in Ovarian Cancer Patients Relative to Normal Levels |
|---|---|---|
| CSE1 chromosome segregation 1-like (yeast) | P55060 | up |
| casein kinase 1, epsilon | P49674 | up |
| v-crk sarcoma virus CT10 oncogene homolog (avian) | P46108 | up |
| topoisomerase (DNA) II alpha. 170 kDa | P11388 | up |
| c-src tyrosine kinase | P41240 | up |
| catechol-O-methyltransferase | P21964 | up |
| WAS protein family, member 1 | Q92558 | up |
| erythrocyte membrane protein band 4.9 (dematin) | Q08495 | up |
| potassium large conductance calcium-activated channel, subfamily M, alpha member 1 | Q12791 | up |
| nuclear receptor coactivator 3 | Q9Y6Q9 | up |
| TEA domain family member 1 (SV40 transcriptional enhancer factor) | P28347 | up |
| peroxisome biogenesis factor 1 | O43933 | up |
| translin-associated factor X | Q99598 | up |
| G protein-coupled receptor 51 | O75899 | up |
| solute carrier family 9 (sodium/hydrogen exchanger), isoform 1 (antiporter, NA+/H+, amiloride sensitive) | P19634 | up |
| integrin, alpha 2 (CD49B, alpha 2 subunit of VLA-2 receptor) | P17301 | up |
| MCM6 minichromosome maintenance deficient 6 (MIS5 homolog, S. pombe) (S. cerevisiae) | Q14566 | up |
| syntaxin 6 | O43752 | up |
| KH domain containing, RNA binding, signal transduction associated 1 | Q07666 | up |
| dystrophia myotonica-protein kinase | Q09013 | up |
| eukaryotic translation initiation factor 4 gamma, 1 | Q04637 | up |
| Rho GDP dissociation inhibitor (GDI) beta | P52566 | up |
| endothelin receptor type A | P25101 | up |
| synaptophysin | P08247 | up |
| transcription factor 3 (E2A immunoglobulin enhancer binding factors E12/E47) | P15923 | up |
| fibronectin 1 | P02751 | up |
| RAS p21 protein activator (GTPase activating protein) 1 | P20936 | up |
| SWI/SNF related, matrix associated, actin dependent regulator of chromatin, subfamily a, member 2 | P51531 | up |
| syntaxin binding protein 5 (tomosyn) | Q5T5C0 | up |
| Ras-GTPase-activating protein SH3-domain-binding protein | Q13283 | up |
| glutamate receptor, ionotropic, N-methyl D-aspartate 2B | Q13224 | up |
| synapsin II | Q92777 | Down |
| sortilin-related receptor, L (DLR class) A repeats-containing | Q92673 | Down |
| excision repair cross-complementing rodent repair deficiency, complementation group 2 (xeroderma pigmentosum D) | P18074 | Down |
| signal transducer and activator of transcription 6, interleukin-4 induced | P42226 | Down |

TABLE 1-continued

Biomarkers for Ovarian Cancer

| Biomarker | Accession No. | Level in Ovarian Cancer Patients Relative to Normal Levels |
|---|---|---|
| tripartite motif-containing 3 | O75382 | Down |
| protein kinase C, theta | Q04759 | Down |
| syntaxin 8 | Q9UNK0 | Down |
| glutamate-ammonia ligase (glutamine synthase) | P15104 | Down |
| protein kinase C, beta 1 | P05771 | Down |
| chromosome condensation 1 | P18754 | Down |
| DEAH (Asp-Glu-Ala-His) box polypeptide 16 | O60231 | Down |
| ribosomal protein L22 | P35268 | Down |
| caveolin 1, caveolae protein, 22 kDa | Q03135 | Down |
| retinoblastoma-like 2 (p130) | Q08999 | Down |
| cyclin-dependent kinase inhibitor 1A (p21, Cip1) | P38936 | Down |
| protein tyrosine phosphatase, receptor-type, Z polypeptide 1 | O76043 | Down |
| general transcription factor II, i | O15359 | Down |
| adaptor-related protein complex 2, alpha 1 subunit | O95782 | Down |
| linker for activation of T cells | O43561 | Down |

TABLE 2

Biomarkers Whose Level Changes are Prominent in Patients with Mucinous, but not Serous, Ovarian Cancer

| Biomarker | Accession No. | Level in Ovarian Cancer Patients Relative to Normal Levels |
|---|---|---|
| non-metastatic cells 1, protein (NM23) | P15531 | up |
| zeta-chain (TCR) associated protein kinase 70 kDa | P43403 | up |
| TATA box binding protein | P20226 | up |
| thyroid autoantigen 70 kDa (Ku antigen) | P12956 | Down |
| 5-hydroxytryptamine (serotonin) receptor 2A | P28223 | Down |

TABLE 3

Biomarkers Whose Levels are Lower in Samples from Patients with Mucinous Ovarian Cancer who Smoke Relative to Patients with Mucinous Ovarian Cancer who Don't Smoke

| Biomarker | Accession No. | Level in Smoking MOC[a] Patients Relative to Nonsmoking MOC Patients |
|---|---|---|
| survival of motor neuron protein interacting protein 1 | O14893 | Down |
| three prime repair exonuclease 1 | Q9BPW1 | Down |
| chromogranin B (secretogranin 1) | P05060 | Down |
| solute carrier family 25 (mitochondrial carrier, Aralar), member 12 | O75746 | Down |
| cyclin-dependent kinase 4 | P11802 | Down |
| likely ortholog of rat F-actin binding protein nexilin | Q0ZGT2 | Down |

[a]MOC = mucinous ovarian cancer

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of diagnostically evaluating a female subject for ovarian cancer, comprising:
   a) obtaining a test biological sample of blood, plasma, or serum from said female subject;
   b) assaying said test biological sample for casein kinase 1, epsilon using an antibody profiling assay;
   c) comparing the results obtained in step b) with the results of an assay of casein kinase 1, epsilon in a control sample;
   wherein an elevated level of autoantibodies specific for casein kinase 1, epsilon in said test biological sample relative to said control sample, is an indication that said subject has ovarian cancer.

2. The method of claim 1, further comprising assaying said biological sample for one or more additional proteins using an antibody profiling assay, wherein an elevated level of autoantibodies specific for said one or more additional proteins is a further indication that said subject has ovarian cancer, and wherein said additional proteins are selected from the group consisting of: CSE1 chromosome segregation 1-like (yeast) (UniProt Knowledgebase sequence P55060);

v-crk sarcoma virus CT10 oncogene homolog (avian) UniProt Knowledgebase sequence P46108); WAS protein family, member 1 (UniProt Knowledgebase sequence Q92558); topoisomerase (DNA) II alpha 170kDa (UniProt Knowledgebase sequence P11388); and integrin, alpha 2 (CD49B, alpha 2 subunit of VLA-2 receptor) (UniProt Knowledgebase sequence P17301).

3. The method of claim 2, wherein a total of at least 5 proteins (including casein kinase 1, epsilon) are assayed.

4. The method of claim 3, wherein said female subject has symptoms suggesting that said female subject may have ovarian cancer.

5. The method of claim 1, further comprising assaying said biological sample for one or more additional proteins using an antibody profiling assay, wherein an elevated level of autoantibodies specific for said one or more additional proteins is a further indication that said subject has ovarian cancer, and wherein said additional proteins are selected from the group consisting of:

erythrocyte membrane protein band 4.9 (dematin) (UniProt Knowledgebase sequence Q08495); potassium large conductance calcium-activated channel, subfamily M, alpha member 1 (UniProt Knowledgebase sequence Q12791); nuclear receptor coactivator 3 (UniProt Knowledgebase sequence Q9Y6Q9); TEA domain family member 1 (SV40 transcriptional enhancer factor) (UniProt Knowledgebase sequence P28347); peroxisome biogenesis factor 1 (UniProt Knowledgebase sequence O43933); translinassociated factor X (UniProt Knowledgebase sequence Q99598); G protein-coupled receptor 51 (UniProt Knowledgebase sequence O75899); solute carrier family 9 (sodium/hydrogen exchanger), isoform 1 (antiporter, NA+/H+, amiloride sensitive) (UniProt Knowledgebase sequence P19634);; MCM6 minichromosome maintenance deficient 6 (MIS5 homolog, S. pombe) (S. cerevisiae) (UniProt Knowledgebase sequence Q14566); syntaxin 6 (UniProt Knowledgebase sequence O43752); KH domain containing, RNA binding, signal transduction associated 1 (UniProt Knowledgebase sequence Q07666); dystrophia myotonica-protein kinase (UniProt Knowledgebase sequence Q09013); eukaryotic translation initiation factor 4 gamma, 1 (UniProt Knowledgebase sequence Q04637); Rho GDP dissociation inhibitor (GDI) beta (UniProt Knowledgebase sequence P52566);

endothelin receptor type A (UniProt Knowledgebase sequence P25101);

synaptophysin (UniProt Knowledgebase sequence P08247); transcription factor 3 (E2A immunoglobulin enhancer binding factors E12/E47) (UniProt Knowledgebase sequence P15923); fibronectin 1 (UniProt Knowledgebase sequence P02751); RAS p21 protein activator (GTPase activating protein) 1 (UniProt Knowledgebase sequence P20936); SWI/SNF related, matrix associated, actin dependent regulator of chromatin, subfamily a, member 2 (UniProt Knowledgebase sequence P51531);

syntaxin binding protein 5 (tomosyn) (UniProt Knowledgebase sequence Q5T5C0);

Ras-GTPase-activating protein SH3-domainbinding protein (UniProt Knowledgebase sequence Q13283); glutamate receptor, ionotropic, N-methyl D-aspartate 2B (UniProt Knowledgebase sequence Q13224); zeta-chain (TCR) associated protein kinase 70kDa (UniProt Knowledgebase sequence P43403); and TATA box binding protein (UniProt Knowledgebase sequence P20226).

6. The method of claim 5, wherein a total of at least 10 proteins (including casein kinase 1, epsilon) are assayed.

7. The method of claim 6, wherein said female subject has symptoms suggesting that said female subject may have ovarian cancer.

8. The method of claim 5, wherein said female subject has symptoms suggesting that said female subject may have ovarian cancer.

9. The method of claim 1, further comprising assaying said biological sample for one or more further proteins using an antibody profiling assay, wherein a reduced level of autoantibodies specific for said one or more further proteins is a further indication that said subject has ovarian cancer, and wherein said further proteins are selected from the group consisting of: synapsin II (UniProt Knowledgebase sequence Q92777); sortilin-related receptor, L (DLR class) A repeats-containing (UniProt Knowledgebase sequence Q92673); excision repair cross-complementing rodent repair deficiency, complementation group 2 (xeroderma pigmentosum D) (UniProt Knowledgebase sequence P18074); and signal transducer and activator of transcription 6, interleukin-4 induced (UniProt Knowledgebase sequence P42226).

10. The method of claim 9, wherein a total of at least 5 proteins (including casein kinase 1, epsilon) are assayed.

11. The method of claim 10, wherein said female subject has symptoms suggesting that said female subject may have ovarian cancer.

12. The method of claim 9, wherein said female subject has symptoms suggesting that said female subject may have ovarian cancer.

13. The method of claim 1, further comprising assaying said biological sample for one or more further proteins using an antibody profiling assay, wherein a reduced level of autoantibodies specific for said one or more further proteins is a further indication that said subject has ovarian cancer, and wherein said further proteins are selected from the group consisting of: tripartite motif containing 3 (UniProt Knowledgebase sequence O75382); protein kinase C, theta (UniProt Knowledgebase sequence Q04759); syntaxin 8 (UniProt Knowledgebase sequence Q9UNK0); glutamate-ammonia ligase (glutamine synthase) (UniProt Knowledgebase sequence P15104); protein kinase C, beta 1 (UniProt Knowledgebase sequence P05771); chromosome condensation 1 (UniProt Knowledgebase sequence P18754); DEAH (Asp-Glu-Ala-His) box polypeptide 16 (UniProt Knowledgebase sequence O60231); ribosomal protein L22 (UniProt Knowledgebase sequence P35268); caveolin 1, caveolae protein, 22kDa (UniProt Knowledgebase sequence Q03135); retinoblastoma-like 2 (p130) (UniProt Knowledgebase sequence Q08999);

cyclin-dependent kinase inhibitor 1A (p21, Cip 1) (UniProt Knowledgebase sequence P38936); protein tyrosine phosphatase, receptor-type, Z polypeptide 1 (UniProt Knowledgebase sequence O76043); general transcription factor II, i (UniProt Knowledgebase sequence O15359); adaptor-related protein complex 2, alpha 1 subunit (UniProt Knowledgebase sequence O95782); linker for activation of T cells (UniProt Knowledgebase sequence O43561); thyroid autoantigen 70kDa (Ku antigen) (UniProt Knowledgebase sequence P12956); and 5-hydroxytryptamine (serotonin) receptor 2A (UniProt Knowledgebase sequence P28223).

14. The method of claim 13, wherein a total of at least 10 proteins (including casein kinase 1, epsilon) are assayed.

15. The method of claim 14, wherein said female subject has been diagnosed as having ovarian cancer or has symptoms suggesting that said female subject may have ovarian cancer.

16. The method of claim 13, wherein said female subject has been diagnosed as having ovarian cancer or has symptoms suggesting that said female subject may have ovarian cancer.

17. The method of claim 1, wherein said female subject has been diagnosed as having ovarian cancer or has symptoms suggesting that said female subject may have ovarian cancer.

18. The method of claim 1, wherein a single autoantibody assay is used to assay said test biological sample and said control sample.

19. The method of claim 18, wherein, in said autoantibody assay, antibodies from said test biological sample are labeled with a first detectable label and antibodies from said control sample are labeled with a second detectable label; wherein said first detectable label and said second detectable labels are dyes or fluorescent labels that absorb or fluoresce at a different wavelengths from one another.

* * * * *